United States Patent
Mallo et al.

(10) Patent No.: US 6,197,287 B1
(45) Date of Patent: Mar. 6, 2001

(54) THICKENING LATEX, MANUFACTURING PROCESS AND COSMETIC APPLICATIONS

(75) Inventors: Paul Mallo, Chatou; Guy Tabacchi; Jean-Pierre Boiteux, both of Castres, all of (FR)

(73) Assignee: Societe d'Exploitation de Produits pour les Industries Chimiques Seppic, Paris Cedex (FR)

( * ) Notice: Subject to any disclaimer, the term of this patent is extended or adjusted under 35 U.S.C. 154(b) by 0 days.

(21) Appl. No.: 09/233,177

(22) Filed: Jan. 19, 1999

(30) Foreign Application Priority Data

| Jan. 16, 1998 | (FR) | 98 00464 |
| Feb. 10, 1998 | (FR) | 98 01525 |
| Aug. 4, 1998 | (FR) | 98 09999 |

(51) Int. Cl.$^7$ ..................................... A61K 7/06
(52) U.S. Cl. ................. 424/70.16; 424/401; 514/844; 514/939; 514/944; 514/945
(58) Field of Search ........................... 514/939, 844, 514/944, 945; 424/401, 70.16

(56) References Cited

U.S. PATENT DOCUMENTS

| 4,539,368 | 9/1985 | Duncan et al. . |
| 4,702,844 | 10/1987 | Flesher et al. . |
| 4,906,701 | 3/1990 | Clark, Jr. . |
| 5,185,395 | 2/1993 | Robinson et al. . |
| 5,472,698 | * 12/1995 | Rawlings et al. . |

FOREIGN PATENT DOCUMENTS

| 0 503 853 | 9/1992 | (EP) . |
| 0 793 957 | 9/1997 | (EP) . |
| 92/03498 | 3/1992 | (WO) . |

* cited by examiner

*Primary Examiner*—Raj Bawa
*Assistant Examiner*—Alysia Berman
(74) *Attorney, Agent, or Firm*—Young & Thompson

(57) ABSTRACT

Composition comprising an oil phase, an aqueous phase, at least one emulsifier of water-in-oil (W/O) type, at least one emulsifier of oil-in-water (O/W) type, characterized in that the composition is an inverted latex comprising from 20% to 60% by weight, and preferably from 25% to 45% by weight, of a branched or crosslinked anionic polyelectrolyte based on at least one monomer possessing a strongly acidic function, copolymerized either with at least one monomer possessing a weakly acidic function or with at least one neutral monomer. The compositions have cosmetic applications.

24 Claims, No Drawings

THICKENING LATEX, MANUFACTURING PROCESS AND COSMETIC APPLICATIONS

FIELD OF THE INVENTION

The present application relates to thickening water-in-oil latices, to a process for their preparation and to their application as thickeners and/or emulsifiers for skincare products and haircare products or for the manufacture of cosmetic, dermopharmaceutical or pharmaceutical preparations.

BACKGROUND OF THE INVENTION

Various thickeners exist and are already used for these purposes. Natural products such as guar gum or corn starch are known in particular, the drawbacks of which are those inherent to natural products, such as price fluctuations, supply difficulties and random quality.

Synthetic polymers in powder form, mainly polyacrylic acids, are also widely used but have the drawback of requiring neutralization when they are used, since they only develop their viscosity from a pH >6.5 and they are often difficult to dissolve.

Synthetic thickening polymers in the form of an inverted latex, that is to say one in which the continuous phase is an oil, are also known. These latices dissolve extremely quickly; the polymers contained in these inverted latices are usually acrylamide/alkali metal acrylate copolymers or acrylamide/sodium 2-acrylamido-2-methylpropane-sulphonate co-polymers; they are already neutralized and when they are dissolved in water, for example to a concentration of 1%, it is observed that the pH is generally above 6.

However, acrylamide/sodium acrylate copolymers do not develop any appreciable thickening properties when the pH is lowered below 6; on the other hand, the acrylamide/sodium 2-acrylamido-2-methylpropane-sulphonate copolymers described in EP 0,503,853 retain an appreciable thickening capacity even at pH 4.

However, such copolymers have monoacrylamide contents which, although extremely low, could result in making them impossible to use in cosmetics in the near future, following changes in the European legislation on hazardous substances.

The Applicant has thus been concerned with the synthesis and development of polymers that thicken, even at acidic pH, in the form of an inverted latex, without using monoacrylamide.

SUMMARY OF THE INVENTION

One subject of the invention is a composition comprising an oil phase, an aqueous phase, at least one emulsifier of water-in-oil (W/O) type, at least one emulsifier of oil-in-water (O/W) type, characterized in that the composition is an inverted latex comprising from 20% to 60% by weight, and preferably from 25% to 45% by weight, of a branched or crosslinked anionic polyelectrolyte based on at least one monomer possessing a strongly acidic function, copolymerized either with at least one monomer possessing a weakly acidic function or with at least one neutral monomer.

The expression "emulsifier of the water-in-oil type" is understood to denote emulsifiers having an HLB value that is low enough to give water-in-oil emulsions, such as the surfactant polymers sold under the name Hypermer™ or such as sorbitan extracts, for instance sorbitan monooleate sold by the company SEPPIC under the tradename Montane 80™, or sorbitan isostearate sold by SEPPIC under the name Montane 70™.

The expression "emulsifier of the oil-in-water type" is understood to denote emulsifiers having an HLB value that is high enough to give oil-in-water emulsions, such as ethoxylated sorbitan esters, for instance sorbitan oleate ethoxylated with 20 mol of ethylene oxide, sold by SEPPIC under the name MONTANOX 80™.

The term branched polymer is understood to denote a non-linear polymer which has pendant chains so as to obtain, when this polymer is dissolved in water, a high degree of entangling leading to very high low-gradient viscosities.

The term crosslinked polymer is understood to denote a non-linear polymer in the form of a three-dimensional network which is insoluble in water but swellable in water and thus leading to the production of a chemical gel.

The composition according to the invention can contain crosslinked units and/or branched units.

The subject of the invention is, in particular, a composition as defined above, characterized in that the anionic polyelectrolyte is the result of a copolymerization of its precursor monomers, which is carried out at a pH below 4.

The subject of the invention is also a composition as defined above, characterized in that 30% to 90% of the monomer units which comprise the anionic polyelectrolyte have a strongly acidic function.

The strongly acidic function of the monomer containing it is, in particular, a sulphonic acid function or a phosphonic acid function, partially or totally salified. The monomer can be for instance, styrenesulfonic acid partially or totally salified. It is preferably 2-methyl-2-[(1-oxo-2-propenyl) amino]-1-propanesulphonic acid partially or totally salified in the form of an alkali metal salt or an ammonium salt. The weakly acidic function of the monomer containing it is, in particular, a carboxylic acid function, and the monomer is preferably chosen from acrylic acid, methacrylic acid, itaconic acid and maleic acid. The neutral monomer is chosen in particular from 2-hydroxyethyl acrylate, 2,3-dihydroxypropyl acrylate, 2-hydroxyethyl methacrylate and 2,3-dihydroxypropyl methacrylate, or an ethoxylated derivative, with a molecular weight between 400 and 1000, of each of these esters.

According to a specific aspect of the present invention, it relates to a composition comprising an oil phase, an aqueous phase, at least one emulsifier of water-in-oil (W/O) type and at least one emulsifier of oil-in-water (O/W) type, characterized in that the said composition is a reverse latex comprising from 20% to 60% by weight, and preferably from 25% to 45% by weight, of a branched or crosslinked, anionic polyelectrolyte based on partially or totally salified 2-methyl-2-[(1-oxo-2-propenyl)amino]-1-propanesulfonic acid, copolymerized with 2-hydroxyethyl acrylate, more particularly, a composition as defined above, characterized in that 30% to 90%, preferably 50% to 90%, in molar proportions, of the monomer units comprised by the anionic polyelectrolyte is 2-methyl-2-[(1-oxo-2-propenyl)amino]-1-propanesulfonic acid (MPSA) partially or totally salified, and in particular a composition as defined above, for which the anionic polyelectrolyte contains, in molar proportions, from 60% to 90% of sodium salt or of ammonium salt of 2-methyl-2[(1-oxo-2-propenyl)amino]-1-propanesulfonic acid and from 10% to 40% of 2-hydroxyethyl acrylate.

According to another specific aspect of the present invention, it relates to a composition as defined above, characterized in that the composition is a reverse latex comprising from 20% to 60% by weight, and preferably from 30% to 45% by weight, of a branched or crosslinked, anionic polyelectrolyte based on a 2-methyl-2-[(1-oxo-2-propenyl)amino]-1-propanesulfonic acid, which is partially or totally salified in the form of sodium salt or of ammonium salt, copolymerized with acrylic acid, partially salified in the form of the sodium salt or of ammonium salt.

The subject of the invention is, more particularly, a composition as defined above, characterized in that the anionic polyelectrolyte is crosslinked and/or branched with a diethylenic or polyethylenic compound in a molar proportion, expressed relative to the monomers used, of from 0.005% to 1% and preferably from 0.01% to 0.2%, and more particularly from 0.01% to 0.1%, and preferably that for which the crosslinking agent and/or the branching agent is chosen from ethylene glycol dimethacrylate, sodium diallyl-oxyacetate, ethylene glycol diacrylate, diallylurea, trimethylolpropane triacrylate or methylene-bisacrylamide.

The latex according to the invention generally contains from 2.5% to 15% by weight, and preferably from 4% to 9% by weight, of emulsifiers, among which from 20% to 50%, in particular from 25% to 40%, of the total weight of the emulsifiers present are of the water-in-oil (W/O) type and in which from 80% to 50%, in particular from 75% to 60%, of the total weight of the emulsifiers are of the oil-in-water (O/W) type.

According to a specific aspect, the composition as defined above is characterized in that the oil phase represents from 15% to 40%, preferably from 20% to 25%, of its total weight.

This oil phase either consists of a commercial mineral oil containing saturated hydrocarbons such as paraffins, isoparaffins or cycloparaffins having, at room temperature, a density of between 0.7 and 0.9 and a boiling point above 180° C., such as, for example, Exxsol™ D 100 S or Marcol™ 52 sold by Exxon Chemical, isohexadecane or isododecane, or consists of a plant oil or a synthetic oil or of a mixture of several of these oils.

According to a preferred aspect of the present invention, the oil phase consists of Marcol™ 52 or of isohexadecane; isohexadecane, which is identified in Chemical Abstracts by the number RN=93685-80-4, is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9). It is marketed in France by the company Bayer. Marcol™ 52 is a commercial oil corresponding to the definition of liquid petroleum jellies in the French Codex. This is a white mineral oil in accordance with the FDA Regulations 21 CFR 172.878 and CFR 178.3620 (a) and it is listed in the USA Pharmacopoeia, US XXIII (1995) and in the European Pharmacopoeia (1993).

The latices contain between 20% and 50% water. The latices according to the invention can also contain various additives such as completing agents, transfer agents or chain-limiting agents.

According to another aspect of the present invention, its subject is a process for preparing the composition as defined above, characterized in that:
  a) an aqueous solution containing the monomers and the optional additives is emulsified in an oil phase in the presence of one or more emulsifiers of water-in-oil type,
  b) the polymerization reaction is initiated by introducing a free-radical initiator into the emulsion formed in a), after which the reaction is left to proceed,
  c) when the polymerization reaction is complete, one or more emulsifiers of oil-in-water type are introduced at a temperature below 50° C.

According to a variant of this process, the reaction medium obtained after step b) is concentrated by distillation before step c) is carried out.

According to a preferred embodiment of the process as defined above, the polymerization reaction is initiated by a redox couple, such as the cumene hydroperoxide/sodium metabisulphite couple, at a temperature below or equal to 10° C., and is then carried out either in a virtually adiabatic manner up to a temperature above or equal to 40° C., more particularly above or equal to 50° C., or by controlling the temperature evolution.

According to another preferred embodiment of the process, the starting aqueous solution is adjusted to a pH below or equal to 4 before step c) is carried out.

The subject of the invention is also the use of the composition as defined above for preparing a cosmetic, dermo-pharmaceutical or pharmaceutical topical composition.

A topical composition according to the invention, intended to be applied to the skin or mucous membranes of humans or animals can consist of a topical emulsion comprising at least one aqueous phase and at least one oil phase. This topical emulsion can be of the oil-in-water type. More particularly, this topical emulsion can consist of a fluid emulsion, such as a fluid gel or milk. The oil phase of the topical emulsion can consist of a mixture of one or more oils.

A topical composition according to the invention can be intended for cosmetic use or can be used to prepare a medical product intended for the treatment of mucous and skin diseases. In the latter case, the topical composition then contains an active principle which can consist, for example, of an anti-inflammatory agent, a muscle relaxant, an antifungal agent or an antibacterial agent.

When the topical composition is used as a cosmetic composition intended to be applied to the skin or mucous membranes, it may or may not contain an active principle, for example a moisturizer, a tanning agent, a sunscreen, an anti-wrinkle agent, a slimming agent, an anti-radical agent, an antiacne agent or an antifungal agent.

A topical composition according to the invention usually contains between 0.1% and 10% by weight of the thickener defined above. The pH of the topical composition is preferably above or equal to 5.

The topical composition can also contain compounds conventionally included in compositions of this type, for example fragrances, preserving agents, dyes, emollients or surfactants.

According to yet another aspect, the invention relates to the use of the novel thickener mentioned above, in accordance with the invention, to thicken and emulsify a topical composition comprising at least one aqueous phase.

The composition according to the invention is an advantageous substitute for those sold under the name Sepigel™ 305 or Sepigel™ 501 by the Applicant, since it also has good compatibility with the other excipients used for the preparation of formulations such as milks, lotions, creams, soaps, baths, balms, shampoos or conditioners. It can also be employed with the Sepigel™.

In particular, the composition is compatible with the concentrates described and claimed in the international publications WO 92/06778, WO 95/04592, WO 95/13863, WO 96/37285, WO 98/22207, WO 98/47610 or in FR 2,734,496, and with the surfactants described in WO 93/08204.

The composition is particularly compatible with Montanov™ 68, Montanov™ 82, Montanov™ 202 or Sepiperl™ N. It can also be used in emulsions of the type described and claimed in EP 0,629,396 and in cosmetically or physiologically acceptable aqueous dispersions with an organopolysiloxane compound chosen, for example, from those described in WO 93/05762 or in WO 93/21316.

The composition can also be used to form cosmetically or physiologically acceptable gels that are aqueous at acidic pH, such as those described in WO 93/07856; it can also be used in combination with nonionic celluloses in order to form, for example, styling gels, such as those described in EP 0,684,024, or alternatively in combination with fatty acid esters of a sugar, in order to form compositions for treating the hair or the skin, such as those described in EP 0,603,019, or alternatively in shampoos or conditioners as described and claimed in WO 92/21316, or, lastly, in combination with an anionic homopolymer such as Carbopol™ in order to form hair-treatment products, such as those described in DE 195 23596.

The composition according to the invention is also compatible with active principles such as, for example, self-tanning agents, for instance dihydroxyacetone (DHA) or antiacne agents, and it can thus be introduced into self-tanning compositions such as those claimed in EP 0,715, 845, EP 0,604,249, EP 0,576,188 or in WO 93/07902.

The composition is also compatible with N-acylated derivatives of amino acids, which allows it to be used in soothing compositions especially for sensitive skin, such as those described or claimed in WO 92/21318, WO 94/27561 or WO 98/09611.

DETAILED DESCRIPTION OF THE INVENTION

The examples which follow are intended to illustrate the present invention.

EXAMPLE 1

Preparation and Properties of the Inverted Latex According to the Invention

A] Preparation a) The following are loaded into a beaker, with stirring
200 g of deionized water
112.1 g of aqueous 48% (by weight) sodium hydroxide solution
278.4 g of 2-methyl-2-[(1-oxo-2-propenyl)amino]-1-propanesulphonic acid
73.1 g of acrylic acid
0.18 g of sodium diethylenetriaminepentaacetate
0.182 g of methylenebisacrylamide
The pH of the aqueous phase described above is adjusted to 3.5 and the amount of aqueous phase is made up to 682 g by adding deionized water.

In parallel, an organic phase is prepared by introducing the following ingredients successively into a stirred beaker:
220 g of isohexadecane
25 g of Montane 80 VG (sorbitan oleate sold by SEPPIC)
0.2 g of azobisisobutyronitrile
The aqueous phase is introduced gradually into the organic phase and is then subjected to vigorous mechanical stirring of ultra-turrax™ type sold by IKA.

The emulsion obtained is then transferred into a polymerization reactor. A large amount of nitrogen is bubbled through the emulsion so as to remove the oxygen, and the resulting emulsion is cooled to about 5–6° C.

5 ml of a solution containing 0.42% (by weight) of cumene hydroperoxide in isohexadecane are then introduced.

After a period which is sufficient to obtain good homogenization of the solution, aqueous sodium metabisulphite solution (0.2 g in 100 ml of water) is then introduced at a rate of 0.5 ml/minute. The introduction is carried out over about 60 minutes.

During this introduction, the temperature in the polymerization reactor is allowed to rise to the final polymerization temperature.

The reaction medium is then held at this temperature for about 90 minutes.

The mixture is cooled to a temperature of about 35° C. and 50 g of sorbitan oleate ethoxylated with 20 mol of ethylene oxide are introduced slowly.

The desired emulsion is obtained.

Evaluation of the properties:
+ viscosity 25° C. of the latex (Brookfield RVT, No. 3 spindle, speed 20): =650 mPa.s
+ viscosity in water containing 2% latex (Brookfield RVT, No. 6 spindle, speed 20): =33,800 mPa.s.
(Brookfield, No. 6 spindle, speed 5): =74,000 mPa.s.

It is observed that the final product is free of acrylamide.

b) Working in the same manner as in paragraph a), starting with:
200 g of deionized water
121.8 g of aqueous 48% (by weight) sodium hydroxide solution
302.66 g of 2-methyl-2-[(1-oxo-2-propenyl)amino]-1-propanesulfonic acid
49.54 g of acrylic acid
0.18 g of sodium diethylenetriaminepentaacetate, and
0.163 g of methylenebisacrylamide.

The desired emulsion is obtained, which has the following characteristics:
+ viscosity in water containing 2% latex
(Brookfield RVT, No. 6 spindle, speed 20): =29,000 mPa.s
(Brookfield, No. 6 spindle, speed 5): =66,000 mPa.s.

It is observed that the final product is also free of acrylamide.

c) The following are loaded into a beaker, with stirring:
608.8 g of a commercial 50% solution of the sodium salt of 2-methyl-2-[(1-oxo-2-propenyl)amino]-1-propanesulfonic acid,
72.6 g of 2-hydroxyethyl acrylate,
0.18 g of sodium diethylenetriamine pentaacetate, and
0.121 g of methylenebis(acrylamide),
the pH of the aqueous phase described above is adjusted to 3.5, by adding 0.7 g of 2-methyl-2-[(1-oxo-2-propenyl)amino]-1-propanesulfonic acid.

In parallel, an organic phase is prepared by introducing the following successively into a stirred beaker:
220 g of isohexadecane,
25 g of Montano X80 VG (sorbitan oleate ethoxylated with 20 mol of ethylene oxide, sold by SEPPIC) and
0.2 g of azobis(isobutyronitrile).
The aqueous phase is introduced gradually into the organic phase and is then subjected to vigorous mechanical stirring with an Ultra-Turrax™ machine sold by IKA.

The emulsion obtained, characterized by a viscosity at 25° C. of 2600 mPa.s (Brookfield RVT, No. 4 spindle, speed 20), is then transferred into a polymerization reactor. The emulsion is subjected to bubbling with nitrogen at a substantial rate so as to remove the oxygen, and is cooled to about 5–6° C.

10 g of a solution containing 1.1% by weight of cumene hydroperoxide active material in isohexadecane are then introduced. After a sufficient time for good homogenization of the solution, 25 g of aqueous sodium metabisulfite solution (0.2% solution) are introduced over about 25 minutes. During this introduction, the temperature in the polymerization reactor is allowed to rise to the final polymerization temperature and the reaction mixture is then maintained for about 90 minutes at this temperature. The mixture is then cooled to a temperature of about 35° C. and 50 g of Montanov™ 80 VG are then introduced slowly.

The desired emulsion is obtained.

Evaluation of the properties:

Viscosity at 20° C. of the latex at 3% in water (Brookfield RVT, No. 6 spindle, speed 20): =36,700 mPa.s; the pH is 5.1.

The pH is lowered to 3.7 and the following result is then obtained: =31,000 mPa.s.

It is observed that the final product is free of acrylamide.

d) Working in the same way as in paragraph a), by lowering the amount of methylenebis(acrylamide) from 0.121 g to 0.091 g, an emulsion is obtained which has the following viscosity characteristics:

Viscosity at 20° C. of the latex at 3% in water (Brookfield RVT, No. 6 spindle, speed 20): =33,000 mPa.s; the pH is 5.2.

After lowering the pH, the following results are obtained:

at pH=4.0, =31,000 mpa.s;

at pH=2.8, =18,300 mPa.s.

It is observed that the final product is free of acrylamide.

e) Working in the same way as in paragraph A), by lowering the amount of methylenebis(acrylamide) from 0.121 g to 0.084 g and that of the 2-hydroxyethyl acrylate from 72.6 g to 53 g, and by increasing the amount of commercial 50% solution of the sodium salt of 2-methyl-2-[(1-oxo-2-propenyl)amino]-1-propanesulfonic acid from 608.8 g to 628 g, an emulsion is obtained which has the following viscosity characteristics:

viscosity at 20° C. of the latex at 3% in water (Brookfield RVT, No. 6 spindle, speed 20): =27,400 mPa.s; the pH is 5.2.

After lowering the pH, the following results are obtained:

at pH=4.0, =27,400 mPa.s;

at pH=2.8, =18,200 mpa.s.

It is observed that the final product is free of acrylamide.

It is observed that the emulsions obtained have a very specific feel sensation at and above 1% polymer in the solution, and that this difference increases as the concentration increases; it is a very fresh feel sensation at the start, which melts completely on the skin, this feel sensation not being experienced at all with the latices of the prior art.

The examples which follow use, without distinction, the emulsions prepared according to one of paragraphs A a) to A e) (which are referred to in the following examples—compound of Example 1).

B] Properties a) "Emulsifying" Power of Fatty Phases

The inverted latex prepared in paragraph A] b) (composition 1) was used to prepare emulsions with different types of a polar or polar fatty substances of plant or synthetic origin. The cream-gels obtained in the various cases are stable and have an entirely homogeneous appearance. Their viscosity is given in the following table:

| Viscosity at 20° C., in mPa · s Brookfield LVT 6 rpm | Oil used for the fatty phase of the cream-gel (3% of composition 1; fatty phase: 10%) distilled water: 87% |
|---|---|
| ≈80,000 | Jojoba oil |
| ≈100,000 | Sweet almond oil |
| ≈80,000 | Squalane |
| ≈100,000 | Dimethicone |
| ≈65,000 | Isohexadecane |
| ≈100,000 | Isononyl isononanoate |
| ≈100,000 | Cetearyl octanoate |
| ≈100,000 | $C_{12}$—$C_{15}$ benzoate |
| ≈100,000 | TG Caprylic/capric |
| ≈90,000 | Liquid paraffin |

Composition 1 thus makes it possible to disperse and stabilize the fatty phases in an aqueous medium, by simple dilution without a neutralization step being necessary.

b) Heat Stability

A cream-gel comprising 2.5% of composition 1 and 20% of cetearyl octanoate was prepared and the viscosity was measured. The results are as follows:

| | Brookfield LVT viscosity, 6 rpm (in mpa · s) (measured at Ta) |
|---|---|
| After 1 day at 40° C. | ≈69,000 |
| After 7 days at 40° C. | ≈68,000 |
| After 1 month at 40° C. | ≈66,000 | c) Influence of the PH on the Viscosity

The viscosity of the cream-gel prepared with composition 1 is very stable to pH in the range pH=6 to pH=9.

d) Compatibility With Solvents

The viscosity (in mPa.s) of gels containing 3% of composition 1 was measured in various cosmetic solvents at several concentrations.

The results given in the following table show that the viscosity of these gels is not affected by the presence of solvents.

| Solvent | 20% | 40% | 60% |
|---|---|---|---|
| Hexylene glycol | ≈100,000 | ≈10,000 | 5000 |
| Ethanol | ≈100,000 | 100,000 | 40,000 |
| Dipropylene glycol | ≈100,000 | 100,000 | 90,000 |
| Butylene glycol | ≈100,000 | ≈100,000 | ≈100,000 |
| Propylene glycol | ≈100,000 | ≈100,000 | ≈100,000 |
| Glycerol | ≈100,000 | ≈100,000 | ≈100,000 | e) Cosmetic formulae are prepared with each of the latices prepared in paragraphs A]c), A]d) and A]e), these formulae comprising:

0.5%, 1%, 1.5%, 2%, 2.5% or 3% latex

5% Simulsol 165,

20% Lanol 1688, 0.5% Sepicide HB water qs 100%.

It is observed that the feel sensation of the emulsions obtained is very specific at and above 1% polymer in the solution and this difference increases as the concentration increases; it is a very fresh feel sensation at the start, which melts completely on the skin, this feel sensation not being experienced at all with the latices of the prior art.

EXAMPLE 2
Care Cream

| | | |
|---|---|---|
| Cyclomethicone: | | 10% |
| Compound of Example 1: | | 0.8% |
| Montanov ™ 68: | | 4.5 |
| Preserving agent: | | 0.65% |
| Lysine: | | 0.025% |
| EDTA (disodium salt): | | 0.05% |
| Xanthan gum: | | 0.2% |
| Glycerol: | | 3% |
| Water: | | qs 100% |

EXAMPLE 3
Care Cream

| | |
|---|---|
| Cyclomethicone: | 10% |
| Compound of Example 1: | 0.8% |
| Montanov ™ 68: | 4.5% |
| Perfluoropolymethyl Isopropyl ether: | 0.5% |
| Preserving agent: | 0.65% |
| Lysine: | 0.025% |
| EDTA (disodium salt): | 0.05% |
| Pumulen ™ TR: | 0.2% |
| Glycerol: | 3% |
| Water: | qs 100% |

EXAMPLE 4
Aftershave Balm

| | FORMULA | |
|---|---|---|
| A | Compound of Example 1: | 1.5% |
| | Water: | qs 100% |
| B | Micropearl ™ M100: | 5.0% |
| | Sepicide ™ CI: | 0.50% |
| | Fragrance: | 0.20% |
| | 95° ethanol: | 10.0% |

PROCEDURE
Add B to A.

EXAMPLE 5
Satin Body Emulsion

| | FORMULA | |
|---|---|---|
| A | Simusol ™ 165: | 5.0% |
| | Lanol ™ 1688: | 8.50% |
| | Karite butter: | 2% |
| | Liquid paraffin: | 6.5% |
| | Lanol ™ 14M: | 3% |
| | Lanol ™ S: | 0.6% |
| B | Water: | 66.2% |
| C | Micropearl ™ M100: | 5% |
| D | Compound of Example 1: | 3% |
| E | Sepicide ™ CI: | 0.3% |
| | Sepicide ™ HB: | 0.5% |
| | Monteine ™ CA: | 1% |
| | Fragrance: | 0.20% |
| | Vitamin E acetate: | 0.20% |

PROCEDURE
Add C to B, emulsify B in A at 70° C. and then add D at 60° C., followed by E at 30° C.

EXAMPLE 6
Body Milk

| | FORMULA | |
|---|---|---|
| A | Simusol ™ 165: | 5.0% |
| | Lanol ™ 1688: | 12.0% |
| | Lanol ™ 14M: | 2.0% |
| | Cetyl alcohol: | 0.3% |
| | Schercemol ™ OP: | 3% |
| B | Water: | qs 100% |
| C | Compound of Example 1: | 0.35% |
| D | Sepicide ™ CI: | 0.2% |
| | Sepicide ™ HB: | 0.5% |
| | Fragrance: | 0.20% |

PROCEDURE
Emulsify B in A at about 75° C.; add C at about 60° C., followed by D at about 30° C.

EXAMPLE 7
O/W Cream

| | FORMULA | |
|---|---|---|
| A | Simulsol ™ 165: | 5.0% |
| | Lanol ™ 1688: | 20.0% |
| | Lanol ™ P: | 1.0% (stabilizing additive) |
| B | Water: | qs 100% |
| C | Compound of Example 1: | 2.50% |
| D | Sepicide ™ CI: | 0.20% |
| | Sepicide ™ HB: | 0.30% |

PROCEDURE
Introduce B into A at about 75° C.; add C at about 60° C., followed by D at 45° C.

EXAMPLE 8
Non-greasy Antisun Gel

| | FORMULA | |
|---|---|---|
| A | Compound of Example 1: | 3.00% |
| | Water: | 30% |
| B | Sepicide ™ CI: | 0.20% |
| | Sepicide ™ HB: | 0.30% |
| | Fragrance: | 0.10% |
| C | Dye: | q.s. |
| | Water: | 30% |
| D | Micropearl ™ M100: | 3.00% |
| | Water: | q.s. 100% |
| E | Silicone oil: | 2.0%. |
| | Parsol ™ MCX: | 5.00% |

PROCEDURE

Introduce B into A; add C, followed by D and then E.

EXAMPLE 9

Antisun Milk

| | FORMULA | |
|---|---|---|
| A | Sepiperl ™ N: | 3.0% |
| | Sesame oil: | 5.0% |
| | Parsol ™ MCX: | 5.0% |
| | λ-Carrageenan | 0.10% |
| B | Water: | q.s. 100% |
| C | Compound of Example 1: | 0.80% |
| D | Fragrance: | q.s. |
| | Preserving agent: | q.s. |

PROCEDURE

Emulsify B in A at 75° C., then add C at about 60° C., followed by D at about 30° C., and adjust the pH if necessary.

EXAMPLE 10

Massage Gel

| | FORMULA | |
|---|---|---|
| A | Compound of Example 1: | 3.5% |
| | Water: | 20.0% |
| B | Dye: | 2 drops/100 g |
| | Water: | q.s. |
| C | Alcohol: | 10% |
| | Menthol: | 0.10% |
| D | Silicone oil: | 5.0% |

PROCEDURE

Add B to A; then add C to the mixture, followed by D.

EXAMPLE 11

Massage Care Gel

| | FORMULA | |
|---|---|---|
| A | Compound of Example 1: | 3.00% |
| | Water: | 30% |
| B | Sepicide ™ CI: | 0.20% |
| | Sepicide ™ HB: | 0.30% |
| | Fragrance: | 0.05% |
| C | Dye: | q.s. |
| | Water: | q.s. 100% |
| D | Micropearl ™ SQL: | 5.0% |
| | Lanol ™ 1688: | 2% |

PROCEDURE

Prepare A; add B, followed by C and then D.

EXAMPLE 12

Radiant-effect Gel

| | FORMULA | |
|---|---|---|
| A | Compound of Example 1: | 4% |
| | Water: | 30% |
| B | Elastine HPM: | 5.0% |

| | -continued | |
|---|---|---|
| | FORMULA | |
| C | Micropearl ™ M100: | 3% |
| | Water: | 5% |
| D | Sepicide ™ CI: | 0.2% |
| | Sepicide ™ HB: | 0.3% |
| | Fragrance: | 0.06% |
| | 50% sodium pyrrolidinonecarboxylate: | 1% |
| | Water: | q.s. 100% |

PROCEDURE

Prepare A; add B, followed by C and then D.

EXAMPLE 3

Body Milk

| | FORMULA | |
|---|---|---|
| A | Sepiperl ™ N: | 3.0% |
| | Glyceryl triheptanoate: | 10.0% |
| B | Water: | q.s. 100% |
| C | Compound of Example 1: | 1.0% |
| D | Fragrance: | q.s. |
| | Preserving agent: | q.s. |

PROCEDURE

Melt A at about 75° C. Emulsify B in A at 75° C. and then add C at about 60° C., followed by D.

EXAMPLE 14

Make-up-removing Emulsion Containing Sweet Almond Oil

| FORMULA | |
|---|---|
| Montanov ™ 68: | 5% |
| Sweet almond oil: | 5% |
| Water: | q.s. 100% |
| Compound of Example 1: | 0.3% |
| Glycerol: | 5% |
| Preserving agent: | 0.2% |
| Fragrance: | 03% |

EXAMPLE 15

Moisturizing Cream for Greasy Skin

| | FORMULA | |
|---|---|---|
| A | Montanov ™ 68: | 5% |
| | Cetylstearyl octanoate: | 8% |
| | Octyl palmitate: | 2% |
| | Water: | q.s. 100% |
| | Compound of Example 1: | 0.6% |
| | Micropearl ™ M100: | 3.0% |
| | Mucopolysaccharides: | 5% |
| | Sepicide ™ HB: | 0.8 |
| | Fragrance: | 03% |

EXAMPLE 16

Alcohol-free, Soothing After-shave Balm

| FORMULA | |
|---|---|
| Mixture of laurylamino acids | 0.1% to 5% |
| Magnesium potassium aspartate: | 0.002% to 0.5% |
| Lanol ™ 99: | 2% |
| Sweet almond oil: | 0.5% |
| Water: | q.s. 100% |
| Compound of Example 1: | 3% |
| Sepicide ™ HB: | 0.3% |
| Sepicide ™ CI: | 0.2% |
| Fragrance: | 0.4% |

EXAMPLE 17

Cream Containing AHAs for Sensitive Skin

| FORMULA | |
|---|---|
| Mixture of laurylamino acids: | 0.1% to 5% |
| Magnesium potassium aspartate: | 0.002% to 0.5% |
| Lanol ™ 99: | 2% |
| Montanov ™ 68: | 5.0% |
| Water: | q.s. 100% |
| Compound of Example 1: | 1.50% |
| Gluconic acid: | 1.50% |
| Triethanolamine: | 0.9% |
| Sepicide ™ HB: | 0.3% |
| Sepicide ™ CI: | 0.2% |
| Fragrance: | 0.4% |

EXAMPLE 18

Aftersun Soothing Care Product

| FORMULA | |
|---|---|
| Mixture of lauryl amino acids: | 0.1% to 5% |
| Magnesium potassium aspartate: | 0.002% to 0.5% |
| Lanol ™ 99: | 10.0% |
| Water: | q.s. 100% |
| Compound of Example 1: | 2.50% |
| Sepicide ™ HB: | 0.3% |
| Sepicide ™ CI: | 0.2% |
| Fragrance: | 0.4% |
| Dye: | 0.03% |

EXAMPLE 19

Make-up-removing Milk

| FORMULA | |
|---|---|
| Sepiperl ™ N: | 3% |
| Primol 352: | 8.0% |
| Sweet almond oil: | 2% |
| Water: | q.s. 100% |
| Compound of Example 1: | 0.8% |
| Preserving agent: | 0.2% |

EXAMPLE 20

Body Milk

| FORMULA | |
|---|---|
| Sepiperl ™ N: | 3.5% |
| Lanol ™ 37T: | 8.0% |
| Solagum ™ L: | 0.05% |
| Water | q.s. 100% |
| Benzophenone: | 2.0% |
| Dimethicone 350cPs: | 0.05% |
| Compound of Example 1: | 0.8% |
| Preserving agent: | 0.2% |
| Fragrance: | 0.4% |

EXAMPLE 21

Alkaline-pH Fluid Emulsion

| | |
|---|---|
| Marcol ™ 82: | 5.0% |
| NaOH: | 10.0% |
| water: | q.s. 100% |
| Compound of Example 1: | 1.5% |

EXAMPLE 22

Fluid Foundation

| FORMULA | |
|---|---|
| Simusol ™ 165: | 5.0% |
| Lanol ™ 84D: | 8.0% |
| Lanol ™ 99: | 5.0% |
| Water: | q.s. 100% |
| Inorganic fillers and pigments: | 10.0% |
| Compound of Example 1: | 1.2% |
| Preserving agent: | 0.2% |
| Fragrance: | 0.4% |

EXAMPLE 23

Antisun Milk

| FORMULA | |
|---|---|
| Sepiperl ™ N: | 3.5% |
| Lanol ™ 37T: | 10.0% |
| Parsol NOX ™ : | 5.0% |
| Eusolex ™ 4360: | 2.0% |
| Water: | q.s. 100% |
| Compound of Example 1: | 1.8% |
| Preserving agent: | 0.2% |
| Fragrance: | 0.4% |

EXAMPLE 24

Gel for Around the Eyes

| FORMULA | |
|---|---|
| Compound of Example 1: | 2.0% |
| Fragrance: | 0.06% |
| Sodium pyrrolidinonecarboxylate: | 0.2% |
| Dow Corning ™ 245 Fluid | 2.0% |
| Water: | q.s. 100% |

EXAMPLE 25
Leave-in Care Composition

| FORMULA | |
|---|---|
| Compound of Example 1: | 1.5% |
| Fragrance: | q.s. |
| Preserving agent: | q.s. |
| Dow Corning ™ X2 8360: | 5.0% |
| Dow Corning ™ Q2 1401: | 15% |
| Water: | q.s. 100% |

EXAMPLE 26
Slimming Gel

| FORMULA | |
|---|---|
| Compound of Example 1: | 5% |
| Ethanol: | 30% |
| Menthol: | 0.1% |
| Caffeine: | 2.5% |
| Extract of butcher's-broom: | 2% |
| Extract of ivy: | 2% |
| Sepicide ™ HP: | 1% |
| Water: | q.s. 100% |

EXAMPLE 27
Alcohol-free, Soothing After-shave Balm

| | FORMULA | |
|---|---|---|
| A | Lipacide ™ PVB: | 1.0% |
| | Lanol ™ 99: | 2.0% |
| | Sweet almond oil: | 0.5% |
| B | Compound of Example 1 | 3.5% |
| C | Water: | q.s. 100% |
| D | Fragrance: | 0.4% |
| | Sepicide ™ HB: | 0.4% |
| | Sepicide ™ CI: | 0.2% |

EXAMPLE 28
Refreshing After-shave Gel

| | FORMULA | |
|---|---|---|
| A | Lipacide ™ PVB: | 0.5% |
| | Lanol ™ 99: | 5.0% |
| | Compound of Example 1 | 2.5% |
| B | Water: | q.s. 100% |
| C | Micropearl ™ LM: | 0.5% |
| | Fragrance: | 0.2% |
| | Sepicide ™ HB: | 0.3% |
| | Sepicide ™ CI: | 0.2% |

EXAMPLE 29
Care Product for Greasy Skin

| | FORMULA | |
|---|---|---|
| A | Micropearl ™ M310: | 1.0% |
| | Compound of Example 1 | 5.0% |
| | Octyl isononanoate: | 4.0% |

-continued

| | FORMULA | |
|---|---|---|
| B | Water: | q.s. 100% |
| C | Sepicontrol ™ A5: | 4.0% |
| | Fragrance: | 0.1% |
| | Sepicide ™ HB: | 0.3% |
| | Sepicide ™ CI: | 0.2% |
| D | Capigel ™ 98: | 0.5% |
| | Water: | 10% |

EXAMPLE 30
Cream Containing AHAs

| | FORMULA | |
|---|---|---|
| A | Montanov ™ 68: | 5.0% |
| | Lipacide ™ PVB: | 1.05% |
| | Lanol ™ 99: | 10.0% |
| B | Water: | q.s. 100% |
| | Gluconic acid: | 1.5% |
| | TEA (triethanolamine): | 0.9% |
| C | Compound of Example 1 | 1.5% |
| D | Fragrance: | 0.4% |
| | Sepicide ™ HB: | 0.2% |
| | Sepicide ™ CI: | 0.4% |

EXAMPLE 31
Non-greasy Self-tanning Product for the Face and the Body

| | FORMULA | |
|---|---|---|
| A | Lanol ™ 2681: | 3.0% |
| | Compound of Example 1 | 2.5% |
| B | Water: | q.s. 100% |
| | Dihydroxyacetone: | 3.0% |
| C | Fragrance: | 0.2% |
| | Sepicide ™ HB: | 0.8% |
| | NaOH (sodium hydroxide): | q.s. pH = 5% |

EXAMPLE 32
Antisun Milk Containing Monoï de Tahiti

| | FORMULA | |
|---|---|---|
| A | Monoï de Tahiti: | 10% |
| | Lipacide ™ PVB: | 0.5% |
| | Compound of Example 1 | 2.2% |
| B | Water: | q.s. 100% |
| C | Fragrance: | 0.1% |
| | Sepicide ™ HB: | 0.3% |
| | Sepicide ™ CI: | 0.1% |
| | Octyl methoxycinnamate: | 4.0% |

EXAMPLE 33
Antisun Care Product for the Face

| | FORMULA | |
|---|---|---|
| A | Cyclomethicone and dimethiconol: | 4.0% |
| | Compound of Example 1 | 3.5% |
| B | Water: | q.s. 100% |

-continued

| | FORMULA | |
|---|---|---|
| C | Fragrance: | 0.1% |
| | Sepicide ™ HB: | 0.3% |
| | Sepicide ™ CI: | 0.21% |
| | Octyl methoxycinnamate: | 5.0% |
| | Titanium mica: | 2.0% |
| | Lactic acid: | q.s. pH = 6.5 |

EXAMPLE 34
Self-tanning Emulsion

| | FORMULA | |
|---|---|---|
| A | Lanol ™ 99: | 15% |
| | Montanov ™ 68: | 5.0% |
| | Octyl para-methoxycinnamate: | 3.0% |
| B | Water: | q.s. 100% |
| | Dihydroxyacetone: | 5.0% |
| | Monosodium phosphate: | 0.2% |
| C | Compound of Example 1 | 0.5% |
| | Fragrance: | 0.3% |
| | Sepicide ™ HB: | 0.8% |
| | NaOH: | q.s. pH = 5 |

EXAMPLE 35
Sheen Gel

| Compound of Example 1 | 1.5% |
|---|---|
| Volatile silicone | 25% |
| Monopropylene glycol | 25% |
| Demineralized water | 10% |
| Glycerol | q.s. 100% |

EXAMPLE 36
Slimming Gel

| Compound of Example 1 | 1.5% |
|---|---|
| Isononyl isononanoate | 2% |
| Caffeine | 5% |
| Ethanol | 40% |
| Micropearl ™ LM | 2% |
| Demineralized water | q.s. 100% |
| Preserving agent, fragrance | q.s. |

EXAMPLE 37
Make-up-removing Milk

| Simulsol ™ 165 | 4% |
|---|---|
| Montanov ™ 202 | 1% |
| Triglyceride caprylate caprate | 15% |
| Pecosil ™ DCT | 1% |
| Demineralized water | q.s. |
| Capigel ™ 98 | 0.5% |
| Compound of Example 1 | 1% |
| Proteol ™ oat | 2% |
| NaOH | q.s. pH 7 |

EXAMPLE 38
Antisun Cream

| Simulsol ™ 165 | 3% |
|---|---|
| Montanov ™ 202 | 2% |
| $C_{12}$—$C_{15}$ benzoate | 8% |
| Pecosil ™ PS 100 | 2% |
| Dimethicone | 2% |
| Cyclomethicone | 5% |
| Octyl methoxycinnamate | 6% |
| Benzophenone-3 | 4% |
| Titanium oxide | 8% |
| Xanthan gum | 0.2% |
| Butylene glycol | 5% |
| Demineralized water | q.s. 100% |
| Compound of Example 1 | 1.5% |
| Preserving agent, fragrance | q.s. |

EXAMPLE 39
Care Gel for Mixed Skin

| Compound of Example 1 | 4% |
|---|---|
| Plant squalane | 5% |
| Dimethicone | 1.5% |
| Sepicontrol ™ A5 | 4% |
| Xanthan gum | 0.3% |
| Water | q.s. 100% |
| Preserving agent, fragrance | q.s. |

EXAMPLE 40
Perfumed Body Mask

| Compound of Example 1 | 1.5% |
|---|---|
| Cyclomethicone | 5% |
| Fragrance | 2% |
| Micropearl ™ M100 | 5% |
| Glycerol | 5% |
| Demineralized water | q.s. 100% |

EXAMPLE 41
Cream with Vitamins

| Simulsol ™ 165 | 5% |
|---|---|
| Montanov ™ 202 | 1% |
| Caprylic/capric triglycerides | 20% |
| Vitamin A palmitate | 0.2% |
| Vitamin E acetate | 1% |
| Micropearl ™ M305 | 1.5% |
| Compound of Example 1 | 0.7% |
| Water | q.s. 100% |
| Preserving agent, fragrance | q.s. |

Montanov™ 68 (cetearyl glucoside) is a self-emulsifying composition as described in WO 92/06778, sold by the company SEPPIC.

Micropearl™ M100 is an ultra-fine powder with a very soft feel sensation and a matt effect, sold by the company Matsumo.

Sepicide™ CI, imidazolinurea, is a preserving agent sold by the company SEPPIC.

Pemulen™ TR is an acrylic polymer sold by Goodrich.

Simulsol™ 165 is self-emulsifying glyceryl stearate, sold by the company SEPPIC.

Lanol™ 1688 is a non-greasy emollient ester sold by the company SEPPIC.

Lanol™ 14M and Lanol™ S are consistency factors sold by the company SEPPIC.

Sepicide ™ HB, which is a mixture of phenoxyethanol, methylparaben, ethylparaben, propylparaben and butylparaben, is a preserving agent sold by the company SEPPIC.

Monteine™ CA is a moisturizer sold by the company SEPPIC.

Schercemol™ OP is a non-greasy emollient ester.

Lanol™ P is a stabilizing additive sold by the company SEPPIC.

Parsol™ MCX is octyl para-methoxycinnamate, sold by the company Givaudan.

Sepiperl™ N is a pearlescent agent, sold by the company SEPPIC, based on a mixture of alkylpolyglucosides such as those described in WO 95/13863.

Micropearl™ SQL is a mixture of microparticles containing squalane, which is released under the action of massaging; it is sold by the company Matsumo.

Lanol™ 99 is isononyl isononanoate, sold by the company SEPPIC.

Lanol™ 37T is glyceryl triheptanoate, sold by the company SEPPIC.

Solagum™ L is a carrageenan sold by the company SEPPIC.

Marcol™ 82 is a liquid paraffin sold by the company ESSO.

Lanol™ 84D is dioctyl malate, sold by the company SEPPIC.

Parsol™ NOX is a sunscreen sold by the company Givaudan.

Eusolex™ 4360 is a sunscreen sold by the company Merck.

Dow Corning™ 245 Fluid is cyclomethicone, sold by the company Dow Corning.

Lipacide™ PVB is a palmitoylated wheat protein hydrolysate sold by the company SEPPIC.

Micropearl™ LM is a mixture of squalane, poly(methyl methacrylate) and menthol, sold by the company SEPPIC.

Sepicontrol™ A5 is a mixture of capryloylglycine, sarcosine and extract of Cinnamon zylanicum, sold by the company SEPPIC, such as those described in International patent application PCT/FR 98/01313 filed on Jun. 23, 1998.

Capigel™ 98 is an acrylate copolymer sold by the company SEPPIC.

Lanol™ 2681 is a coconut caprylate/caprate mixture sold by the company SEPPIC.

Montanov™ 202 is an APG/fatty alcohol composition as described in W09 98/47610, sold by the company SEPPIC.

What is claimed is:

1. Composition comprising an oil phase, an aqueous phase, at least one water-in-oil emulsifier, at least one oil-in-water emulsifier, wherein the composition is an inverted latex comprising from 20% to 60% by weight of a branched or crosslinked anionic polyelectrolyte from at least one monomer possessing a strongly acidic function, copolymerized either with at least one monomer possessing a weakly acidic function or with at least one neutral monomer; the strongly acidic function of the monomer containing it being a sulfonic acid function or a phosphonic acid function, partially or totally salified; the weakly acidic function of the monomer containing it being a carboxylic acid function, and the monomer being selected from the group consisting of acrylic acid, methacrylic acid, itaconic acid and maleic acid, partially or totally salified; the neutral monomer being selected from the group consisting of 2-hydroxyethyl acrylate, 2,3-dihydroxypropyl acrylate, 2-hydroxyethyl methacrylate, 2,3-dihydroxypropyl methacrylate, and an ethoxylated derivative, with a molecular weight between 400 and 1000, of each of these esters, the anionic polyelectrolyte being crosslinked and/or branched with a diethylenic or polyethylenic compound in a molar proportion, expressed relative to the monomers used, of from 0.005% to 1%; and wherein 30% to 906 of the monomer units which comprise the anionic polyelectrolyte have a strongly acidic function.

2. The composition according to claim 1, comprising from 25 to 45% by weight of the branched or crosslinked anionic polyelectrolyte.

3. The composition according to claim 1, wherein the anionic polyelectrolyte is the result of a copolymerization of its precursor monomers, which is carried out at a pH less than 4.

4. The composition according to claim 1, wherein 50% to 90% of the monomer units which comprise the anionic polyelectrolyte have a strongly acidic function.

5. The composition according to claim 1, wherein the branched or crosslinked anionic polyelectrolyte is formed from partially or totally salified 2-methyl-2-[(1-oxo-2-propenyl)amino]-1-propanesulfonic acid, copolymerized with 2-hydroxyethyl acrylate.

6. The composition according to claim 5, wherein 30 to 90% in molar proportions of the monomer units comprised by the anionic polyelectrolyte is 2-methyl-2-[(1-oxo-2-propenyl)amino]-1-propanesulfonic acid partially or totally salified in the form of an alkali metal salt or an ammonium salt, and the anionic polyelectrolyte includes, in molar proportions, from 60% to 90% of sodium or of ammonium salt of 2-methyl-2-[(1-oxo-2-propenyl)amino]-1-propanesulfonic acid and from 10% to 40% of 2-hydroxyethyl acrylate.

7. The composition according to claim 1, wherein the inverted latex comprises from 30% to 45% by weight, of a branched or crosslinked, anionic polyelectrolyte based on a 2-methyl-2-[(1-oxo-2-propenyl)amino]-1-propanesulfonic acid which is partially or totally salified in the form of a sodium salt or of the ammonium salt copolymerized with acrylic acid, partially salified in the form of the sodium salt or of the ammonum salt.

8. The composition according to claim 1, wherein the molar proportion ranges from 0.01% to 0.2%.

9. The composition according to claim 1, wherein the crosslinking agent and/or the branching agent is selected from the group consisting of ethylene glycol diacrylate, sodium diallyloxyacetate, ethylene glycol diacrylate, diallylurea, trimethylolpropane triacrylate, and methylenebisacrylamide.

10. The composition according to claim 1, further comprising from 2.5% to 15% by weight of emulsifiers.

11. The composition according to claim 10, comprising from 4% to 9% by weight of emulsifiers.

12. The composition according to claim 10, wherein from 20% to 50% of the total weight of the emulsifiers present are water-in-oil emulsifiers, and from 80% to 50% of the total weight of the emulsifiers are oil-in-water emulsifiers.

13. The composition according to claim 12, wherein from 25% to 40% of the total weight of the emulsifiers present are water-in-oil emulsifiers and from 75% to 60% of the total weight of the emulsifiers are oil-in-water emulsifiers.

14. The composition according to claim 1, wherein the oil phase represents from 15% to 40% of its total weight.

15. The composition according to claim 14, wherein the oil phase represents from 20% to 25% of its total weight.

16. The composition according to claim 14, wherein the oil phase is made up of isohexadecane or white mineral oil.

17. The composition according to claim 1, further comprising one or more additives selected from the group consisting of complexing agents, transfer agents and chain-limiting agents.

18. Process for preparing a composition comprising an oil phase, an aqueous phase, at least one water-in-oil emulsifier, at least one oil-in-water emulsifier, wherein the composition is an inverted latex comprising from 20% to 60% by weight of a branched or crosslinked anionic polyelectrolyte formed from at least one monomer possessing a strongly acidic function, copolymerized either with at least one monomer possessing a weakly acid function or with at least one neutral monomer, the process comprising:
   a) emulsifying an aqueous solution containing the monomers and additives in an oil phase in the presence of one or more water-in-oil emulsifiers;
   b) initiating a polymerization reaction by introducing a free-radical initiator into the emulsion formed in a), and thereafter allowing the reaction to proceed to obtain a reaction medium; and
   c) when the polymerization reaction is complete, introducing one or more oil-in-water emulsifiers at a temperature below 50° C.

19. The process according to claim 18, further comprising concentrating the reaction medium obtained after step b) by distillation before step c) is carried out.

20. The process according to claim 18, wherein the polymerization reaction is initiated by a redox couple at a temperature below or equal to 10° C., and is then carried out in a virtually adiabatic manner to a temperature greater than or equal to 40° C.

21. The process according to claim 18, wherein the starting aqueous solution is adjusted to a pH less than or equal to 4 before step c) is carried out.

22. Cosmetic, dermal-pharmaceutical or pharmaceutical composition comprising from 0.1% to 10% by weight of an inverted latex as defined in claim 1.

23. The cosmetic composition according to claim 22, in the form of a milk, lotion, gel, cream, cream-gel, soap, foam bath, balm, shampoo or conditioner.

24. A soothing composition for sensitive skin, comprising an oil phase, an aqueous phase, at least one water-in-oil emulsifier, at least one oil-in-water emulsifier, the composition being an inverted latex comprising from 20% to 60% by weight of a branched or crosslinked anionic polyelectrolyte formed from at least one monomer possessing a strongly acidic function, copolymerized either with at least one monomer possessing a weakly acidic function or with at least one neutral monomer; the soothing composition further comprising one or more N-acylated amino acids.

* * * * *

(12) EX PARTE REEXAMINATION CERTIFICATE (7434th)
United States Patent
Mallo et al.

(10) Number: US 6,197,287 C1
(45) Certificate Issued: Mar. 30, 2010

(54) THICKENING LATEX, MANUFACTURING PROCESS AND COSMETIC APPLICATIONS

(75) Inventors: Paul Mallo, Chatou (FR); Guy Tabacchi, Castres (FR); Jean-Pierre Boiteux, Castres (FR)

(73) Assignee: Societe d'Exploitation de Produits Pour les Industries Chimiques SEPPIC, Paris Cedex (FR)

Reexamination Request:
No. 90/007,509, Apr. 15, 2005
No. 90/007,636, Jul. 20, 2005

Reexamination Certificate for:
Patent No.: 6,197,287
Issued: Mar. 6, 2001
Appl. No.: 09/233,177
Filed: Jan. 19, 1999

(30) Foreign Application Priority Data

Jan. 16, 1998 (FR) .............................. 98 00464
Feb. 10, 1998 (FR) .............................. 98 01525
Aug. 4, 1998 (FR) .............................. 98 09999

(51) Int. Cl.
*C08L 101/00* (2006.01)
*C08F 2/32* (2006.01)

(52) U.S. Cl. .................. 424/70.16; 424/401; 514/844; 514/939; 514/944; 514/945

(58) Field of Classification Search ............... None
See application file for complete search history.

(56) References Cited

U.S. PATENT DOCUMENTS

| | | | |
|---|---|---|---|
| 3,624,019 A | | 11/1971 | Anderson et al. |
| 3,734,873 A | | 5/1973 | Anderson et al. |
| 4,742,086 A | | 5/1988 | Masamizu et al. |
| 5,126,395 A | | 6/1992 | End et al. |
| 5,185,395 A | * | 2/1993 | Robinson et al. ............. 524/457 |
| 5,472,698 A | * | 12/1995 | Rawlings et al. ............. 424/401 |
| 5,484,843 A | | 1/1996 | Mallo et al. ................. 524/804 |
| 5,783,176 A | * | 7/1998 | Meiring et al. ................. 424/64 |
| 5,952,395 A | | 9/1999 | Lorant |

FOREIGN PATENT DOCUMENTS

| | | |
|---|---|---|
| EP | 0 161 038 | 11/1985 |
| EP | 0 186 361 | 7/1986 |
| EP | 0 645 429 | 3/1995 |
| EP | 0 503 853 | 5/1996 |
| EP | 0 503 853 | 5/1998 |
| EP | 1 369 435 | 12/2003 |
| GB | 2007238 A | 5/1979 |
| JP | 9-157130 | 6/1997 |
| JP | 9-157 130 | 6/1997 |
| JP | 10-103293 | 4/1998 |
| WO | WO 92/21318 | 12/1992 |
| WO | WO 99/36445 | 7/1999 |

OTHER PUBLICATIONS

CAS Registry No. 15214–89–8 1–Propanesulfonic acid, 2–methyl–2–[(1–oxo–2–propen–1–yl)amino]–.*
Kirk–Othmer encyclopedia of Chemical Technology, John Wiley & Sons, Inc., 2001, Emulsions and Surfactants.*
Translation of JP Office Action "Reasons for Rejection", dated Aug. 26, 2008, for JP Appln. No. 2000–540160.
Lovell, P.A. et al., "Emulsion Polymerization and Emulsion Polymers", John Wiley and Sons, Chichester, England, 1997, pp. 726–734.
Lovell, P.A. et al., "Emulsion Polymerization a Emulsion Polymerization and Emulsion Polymers", John Wiley and Sons, Chichester, England 1997, pp. 726–734.

* cited by examiner

*Primary Examiner*—Sharon L Turner

(57) ABSTRACT

Composition comprising an oil phase, an aqueous phase, at least one emulsifier of water-in-oil (W/O) type, at least one emulsifier of oil-in-water (O/W) type, characterized in that the composition is an inverted latex comprising from 20% to 60% by weight, and preferably from 25% to 45% by weight, of a branched or crosslinked anionic polyelectrolyte based on at least one monomer possessing a strongly acidic function, copolymerized either with at least one monomer possessing a weakly acidic function or with at least one neutral monomer. The compositions have cosmetic applications.

US 6,197,287 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–4, 7–12, 14, 17–19 and 22–24 are cancelled.

Claims 5, 13, 15, 16, 20 and 21 are determined to be patentable as amended.

Claims 6, dependent on an amended claim, is determined to be patentable.

5. [The composition according to claim 1] *Composition comprising an oil phase, an aqueous phase, at least one water-in-oil emulsifier, at least one oil-in-water emulsifier, wherein the composition is an inverted latex comprising from 20% to 60% by weight of a branched or crosslinked anionic polyelectrolyte from at least one monomer possessing a strongly acidic function, copolymerized either with at least one monomer possessing a weakly acidic function or with at least one neutral monomer; the strongly acidic function of the monomer containing it being a sulfonic acid function or a phosphonic acid function, partially or totally salified; the weakly acidic function of the monomer containing it being a carboxylic acid function, and the monomer being selected from the group consisting of acrylic acid, methacrylic acid, itaconic acid and maleic acid, partially or totally salified; the neutral monomer being selected from the group consisting of 2-hydroxyethyl acrylate, 2,3-dihydroxypropyl acrylate, 2-hydroxyethyl methacrylate, 2,3-dihydroxypropyl methacrylate, and an ethoxylated derivative, with a molecular weight between 400 and 1000, of each of these esters, the anionic polyelectrolyte being crosslinked and/or branched with a diethylenic or polyethylenic compound in a molar proportion, expressed relative to the monomers used, of from 0.005% to 1%; and wherein 30% to 90% of the monomer units which comprise the anionic polyelectrolyte have a strongly acidic function*, wherein the branched or crosslinked anionic polyelectrolyte is formed from partially or totally salified 2-methyl-2-[(1-oxo-2-propenyl)amino]-1-propanesulfonic acid, copolymerized with 2-hydroxyethyl acrylate.

13. [The composition according to claim 12] *Composition comprising an oil phase, an aqueous phase, at least one water-in-oil emulsifier, at least one oil-in-water emulsifier, wherein the composition is an inverted latex comprising from 20% to 60% by weight of a branched or crosslinked anionic polyelectrolyte from at least one monomer possessing a strongly acidic function, copolymerized either with at least one monomer possessing a weakly acidic function or with at least one neutral monomer; the strongly acidic function of the monomer containing it being a sulfonic acid function or a phosphonic acid function, partially or totally salified; the weakly acidic function of the monomer containing it being a carboxylic acid function, and the monomer being selected from the group consisting of acrylic acid, methacrylic acid, itaconic acid and maleic acid, partially or totally salified; the neutral monomer being selected from the group consisting of 2-hydroxyethyl acrylate, 2,3-dihydroxypropyl acrylate, 2-hydroxyethyl methacrylate, 2,3-dihydroxypropyl methacrylate, and an ethoxylated derivative, with a molecular weight between 400 and 1000, of each of these esters, the anionic polyelectrolyte being crosslinked and/or branched with a diethylenic or polyethylenic compound in a molar proportion, expressed relative to the monomers used, of from 0.005% to 1%; and wherein 30% to 90% of the monomer units which comprise the anionic polyelectrolyte have a strongly acidic function, wherein said composition comprises from 2.5% to 15% by weight of emulsifiers and wherein from 20% to 50% of the total weight of the emulsifiers present are water-in-oil emulsifiers, and from 80% to 50% of the total weight of the emulsifiers are oil-in-water emulsifiers*, wherein from 25% to 40% of the total weight of the emulsifiers present are water-in-oil emulsifiers and from 75% to 60% of the total weight of the emulsifiers are oil-in-water emulsifiers.

15. [The composition according to claim 14] *Composition comprising an oil phase, an aqueous phase, at least one water-in-oil emulsifier, at least one oil-in-water emulsifier, wherein the composition is an inverted latex comprising from 20% to 60% by weight of a branched or crosslinked anionic polyelectrolyte from at least one monomer possessing a strongly acidic function, copolymerized either with at least one monomer possessing a weakly acidic function or with at least one neutral monomer; the strongly acidic function of the monomer containing it being a sulfonic acid function or a phosphonic acid function, partially or totally salified; the weakly acidic function of the monomer containing it being a carboxylic acid function, and the monomer being selected from the group consisting of acrylic acid, methacrylic acid, itaconic acid and maleic acid, partially or totally salified; the neutral monomer being selected from the group consisting of 2-hydroxyethyl acrylate, 2,3-dihydroxypropyl acrylate, 2-hydroxyethyl methacrylate, 2,3-dihydroxypropyl methacrylate, and an ethoxylated derivative, with a molecular weight between 400 and 1000, of each of these esters, the anionic polyelectrolyte being crosslinked and/or branched with a diethylenic or polyethylenic compound in a molar proportion, expressed relative to the monomers used, of from 0.005% to 1%; and wherein 30% to 90% of the monomer units which comprise the anionic polyelectrolyte have a strongly acidic function*, wherein the oil phase represents from 20% to 25% of [its] *the* total weight *of said composition*.

16. [The composition according to claim 14] *Composition comprising an oil phase, an aqueous phase, at least one water-in-oil emulsifier, at least one oil-in-water emulsifier, wherein the composition is an inverted latex comprising from 20% to 60% by weight of a branched or crosslinked anionic polyelectrolyte from at least one monomer possessing a strongly acidic function, copolymerized either with at least one monomer possessing a weakly acidic function or with at least one neutral monomer; the strongly acidic function of the monomer containing it being a sulfonic acid function or a phosphonic acid function, partially or totally salified; the weakly acidic function of the monomer containing it being a carboxylic acid function, and the monomer being selected from the group consisting of acrylic acid, methacrylic acid, itaconic acid and maleic acid, partially or totally salified; the neutral monomer being selected from the* group consisting of 2-hydroxyethyl acrylate, 2,3-dihydroxypropyl acrylate, 2-hydroxyethyl methacrylate, 2,3-dihydroxypropyl methacrylate, and an ethoxylated derivative, with a molecular weight between 400 and 1000, of each of these esters, the anionic polyelectrolyte being crosslinked and/or branched with a diethylenic or polyethylenic compound in a molar proportion, expressed relative to the monomers used, of from 0.005% to 1%; and wherein 30% to 90% of the monomer units which comprise the anionic polyelectrolyte have a strongly acidic function, wherein the oil phase represents from 15% to 40% of the total weight of said composition, and wherein the oil phase is made up of isohexadecane or white mineral oil.

20. [The process according to claim 18] *Process for preparing a composition comprising an oil phase, an aqueous phase, at least one water-in-oil emulsifier, at least one oil-in-water emulsifier, wherein the composition is an inverted latex comprising from 20% to 60% by weight of a branched or crosslinked anionic polyelectrolyte formed from at least one monomer possessing a strongly acidic function, copolymerized either with at least one monomer possessing a weakly acid function or with at least one neutral monomer, the process comprising:*

*a) emulsifying an aqueous solution containing the monomers and additives in an oil phase in the presence of one or more water-in-oil emulsifiers;*

*b) initiating a polymerization reaction by introducing a free-radical initiator into the emulsion formed in a), and thereafter allowing the reaction to proceed to obtain a reaction medium; and*

*c) when the polymerization reaction is complete, introducing one or more oil-in-water emulsifiers at a temperature below 50° C., wherein the polymerization reaction is initiated by a redox couple at a temperature below or equal to 10° C., and is then carried out in a virtually adiabatic manner to a temperature greater than or equal to 40° C.*

21. [The process according to claim 18] *Process for preparing a composition comprising an oil phase, an aqueous phase, at least one water-in-oil emulsifier, at least one oil-in-water emulsifier, wherein the composition is an inverted latex comprising from 20% to 60% by weight of a branched or crosslinked anionic polyelectrolyte formed from at least one monomer possessing a strongly acidic function, copolymerized either with at least one monomer possessing a weakly acid function or with at least one neutral monomer, the process comprising:*

*a) emulsifying an aqueous solution containing the monomers and additives in an oil phase in the presence of one or more water-in-oil emulsifiers;*

*b) initiating a polymerization reaction by introducing a free-radical initiator into the emulsion formed in a), and thereafter allowing the reaction to proceed to obtain a reaction medium; and*

*c) when the polymerization reaction is complete, introducing one or more oil-in-water emulsifiers at a temperature below 50° C., wherein the starting aqueous solution is adjusted to a pH less than or equal to 4 before step c) is carried out.*

* * * * *

(12) EX PARTE REEXAMINATION CERTIFICATE (9043rd)
United States Patent
Mallo et al.

(10) Number: US 6,197,287 C2
(45) Certificate Issued: May 29, 2012

(54) THICKENING LATEX, MANUFACTURING PROCESS AND COSMETIC APPLICATIONS

(75) Inventors: Paul Mallo, Chatou (FR); Guy Tabacchi, Castres (FR); Jean-Pierre Boiteux, Castres (FR)

(73) Assignee: Societe d'Exploitation de Produits pour les Industries Chimiques Seppic, Paris Cedex (FR)

Reexamination Request:
No. 90/011,149, Sep. 17, 2010

Reexamination Certificate for:
Patent No.: 6,197,287
Issued: Mar. 6, 2001
Appl. No.: 09/233,177
Filed: Jan. 19, 1999

Reexamination Certificate C1 6,197,287 issued Mar. 30, 2011

(30) Foreign Application Priority Data

| Jan. 16, 1998 | (FR) | 98 00464 |
| Feb. 10, 1998 | (FR) | 98 01525 |
| Aug. 4, 1998 | (FR) | 98 09999 |

(51) Int. Cl.
*C08L 101/00* (2006.01)
*C08F 2/32* (2006.01)

(52) U.S. Cl. .............. 424/70.16; 424/401; 514/844; 514/939; 514/944; 514/945

(58) Field of Classification Search .............. 424/70
See application file for complete search history.

(56) References Cited

To view the complete listing of prior art documents cited during the proceeding for Reexamination Control Number 90/011,149, please refer to the USPTO's public Patent Application Information Retrieval (PAIR) system under the Display References tab.

*Primary Examiner* — Sharon Turner

(57) ABSTRACT

Composition comprising an oil phase, an aqueous phase, at least one emulsifier of water-in-oil (W/O) type, at least one emulsifier of oil-in-water (O/W) type, characterized in that the composition is an inverted latex comprising from 20% to 60% by weight, and preferably from 25% to 45% by weight, of a branched or crosslinked anionic polyelectrolyte based on at least one monomer possessing a strongly acidic function, copolymerized either with at least one monomer possessing a weakly acidic function or with at least one neutral monomer. The compositions have cosmetic applications.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-4, 7-12, 14, 17-19 and 22-24 were previously cancelled.

Claim 20 is cancelled.

Claims 5-6, 13, 15-16 and 21 were not reexamined.

* * * * *

(12) EX PARTE REEXAMINATION CERTIFICATE (10760th)
United States Patent
Mallo et al.

(10) Number: US 6,197,287 C3
(45) Certificate Issued: Nov. 9, 2015

(54) THICKENING LATEX, MANUFACTURING PROCESS AND COSMETIC APPLICATIONS

(75) Inventors: Paul Mallo, Chatou (FR); Guy Tabacchi, Castres (FR); Jean-Pierre Boiteux, Castres (FR)

(73) Assignee: SOCIETE D'EXPLOITATION DE PRODUITS POUR LES INDUSTRIES CHIMIQUES SEPPIC, Paris (FR)

Reexamination Request:
No. 90/007,509, Apr. 15, 2005
No. 90/007,636, Jul. 20, 2005

Reexamination Certificate for:
Patent No.: 6,197,287
Issued: Mar. 6, 2001
Appl. No.: 09/233,177
Filed: Jan. 19, 1999

Reexamination Certificate C1 6,197,287 issued Mar. 30, 2010

Reexamination Certificate C2 6,197,287 issued May 29, 2012

(30) Foreign Application Priority Data

| Jan. 16, 1998 | (FR) | 98 00464 |
| Feb. 10, 1998 | (FR) | 98 01525 |
| Aug. 4, 1998 | (FR) | 98 09999 |

(51) Int. Cl.
| *C08F 2/32* | (2006.01) |
| *C08L 101/00* | (2006.01) |
| *A61Q 11/00* | (2006.01) |
| *A61K 8/60* | (2006.01) |

(52) U.S. Cl.
CPC ............... *A61Q 11/00* (2013.01); *A61K 8/602* (2013.01)

(58) Field of Classification Search
None
See application file for complete search history.

(56) References Cited

To view the complete listing of prior art documents cited during the proceedings for Reexamination Control Numbers 90/007,509 and 90/007,636, please refer to the USPTO's public Patent Application Information Retrieval (PAIR) system under the Display References tab.

*Primary Examiner* — Sharon Turner

(57) ABSTRACT

Composition comprising an oil phase, an aqueous phase, at least one emulsifier of water-in-oil (W/O) type, at least one emulsifier of oil-in-water (O/W) type, characterized in that the composition is an inverted latex comprising from 20% to 60% by weight, and preferably from 25% to 45% by weight, of a branched or crosslinked anionic polyelectrolyte based on at least one monomer possessing a strongly acidic function, copolymerized either with at least one monomer possessing a weakly acidic function or with at least one neutral monomer. The compositions have cosmetic applications.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 20 was previously cancelled.

Claims 1-4, 7-19 and 21-24 are cancelled.

Claim 5 is determined to be patentable as amended.

Claim 6, dependent on an amended claim, is determined to be patentable.

5. [The composition according to claim 1] *Composition comprising an oil phase, an aqueous phase, at least one water-in-oil emulsifier, at least one oil-in-water emulsifier, wherein the composition is an inverted latex comprising from 20% to 60% by weight of a branched or crosslinked anionic polyelectrolyte from at least one monomer possessing a strongly acidic function, copolymerized either with at least one monomer possessing a weakly acidic function or with at least one neutral monomer; the strongly acidic function of the monomer containing it being a sulfonic acid function or a phosphonic acid function, partially or totally salified; the weakly acidic function of the monomer containing it being a carboxylic acid function, and the monomer being selected from the group consisting of acrylic acid, methacrylic acid, itaconic acid and maleic acid, partially or totally salified; the neutral monomer being selected from the group consisting of 2-hydroxyethyl acrylate, 2,3-dihydroxypropyl acrylate, 2-hydroxyethyl methacrylate, 2,3-dihydroxypropyl methacrylate, and an ethoxylated derivative, with a molecular weight between 400 and 1000, of each of these esters, the anionic polyelectrolyte being crosslinked and/or branched with a diethylenic or polyethylenic compound in a molar proportion, expressed relative to the monomers used, of from 0.005% to 1%; and wherein 30% to 90% of the monomer units which comprise the anionic polyelectrolyte have a strongly acidic function, wherein the branched or crosslinked anionic polyelectrolyte is formed from partially or totally salified 2-methyl-2-[(1-oxo-2-propenyl)amino]-1-propanesulfonic acid, copolymerized with 2-hydroxyethyl acrylate.*

\* \* \* \* \*